United States Patent
Mackay et al.

(10) Patent No.: US 11,206,851 B2
(45) Date of Patent: *Dec. 28, 2021

(54) PROCESS FOR PRODUCING PROTEIN CONCENTRATE OR ISOLATE AND CELLULOSIC THERMOCHEMICAL FEEDSTOCK FROM BREWERS SPENT GRAINS

(71) Applicant: Zea10 LLC, Eden Prairie, MN (US)

(72) Inventors: Ian Mackay, Eden Prairie, MN (US); Karl Greden, Hinckley, MN (US)

(73) Assignee: Zea 10, LLC, Eden Prairie, MN (US)

( * ) Notice: Subject to any disclaimer, the term of this patent is extended or adjusted under 35 U.S.C. 154(b) by 103 days.

This patent is subject to a terminal disclaimer.

(21) Appl. No.: 15/715,121

(22) Filed: Sep. 25, 2017

(65) Prior Publication Data
US 2018/0199593 A1    Jul. 19, 2018

Related U.S. Application Data

(60) Provisional application No. 62/447,383, filed on Jan. 17, 2017.

(51) Int. Cl.
| | | |
|---|---|---|
| *A23K 20/189* | (2016.01) | |
| *A23K 10/38* | (2016.01) | |
| *C12P 19/02* | (2006.01) | |
| *C12P 19/14* | (2006.01) | |
| *C12P 21/06* | (2006.01) | |
| *C13K 1/06* | (2006.01) | |

(52) U.S. Cl.
CPC ............ *A23K 10/38* (2016.05); *A23K 20/189* (2016.05); *C12P 19/02* (2013.01); *C12P 19/14* (2013.01); *C12P 21/06* (2013.01); *C12Y 302/01003* (2013.01); *C12Y 304/21014* (2013.01); *C12Y 304/21062* (2013.01); *C13K 1/06* (2013.01); *Y02E 50/30* (2013.01); *Y02P 60/87* (2015.11)

(58) Field of Classification Search
CPC ....... A23K 20/189; A23K 10/38; C12P 19/02; C12P 19/14; C12P 21/06; C12Y 302/01003; C12Y 304/21062; C13K 1/06; Y02P 60/873; Y02E 50/343
USPC ....................................................... 426/530
See application file for complete search history.

(56) References Cited

U.S. PATENT DOCUMENTS

| | | | | |
|---|---|---|---|---|
| 3,212,902 | A * | 10/1965 | Bavisotto ............... | A23K 10/14 426/31 |
| 4,341,805 | A * | 7/1982 | Chaudhary ............. | A23L 33/21 426/29 |
| 5,716,801 | A * | 2/1998 | Nielsen ................... | A23J 3/346 426/44 |
| 6,183,640 | B1 * | 2/2001 | Wang ................. | B01D 67/0011 210/500.27 |
| 6,365,395 | B1 * | 4/2002 | Antoniou ............. | B01D 61/142 210/767 |
| 2004/0167019 | A1 * | 8/2004 | Liang ................. | B01D 17/0202 502/433 |
| 2005/0269265 | A1 * | 12/2005 | DeFrees ............... | B01D 61/022 210/639 |
| 2009/0087492 | A1 * | 4/2009 | Johnson ................... | A61K 9/14 424/489 |
| 2010/0196979 | A1 * | 8/2010 | Birkmire ................... | C08H 8/00 435/161 |
| 2011/0263916 | A1 * | 10/2011 | Bao .......................... | C01B 3/38 585/254 |
| 2012/0302731 | A1 * | 11/2012 | Li ............................. | A23J 3/34 530/344 |
| 2013/0323401 | A1 * | 12/2013 | Samoto .................... | A23J 3/16 426/656 |

OTHER PUBLICATIONS

NPL Mussatto et al. (in J Sci. Food Agric. 94: 1264-1275, 2014). (Year: 2014).*
NPL Tang et al. (in J Food Sci. 68 (22): pp. 471-475, 2003) (Year: 2003).*
NPL Hernandez et al. (in JAOCS 77 (2): pp. 177-180, 2000) (Year: 2000).*
NPL Niemi et al. (in Bioresource Technology 136: 529-534, 2013 (Year: 2013).*
NPL Membrane System (in Koch 2004 micron vs kDa MW and membrane filter fig ) . date 2004 https://www.safewater.org/factsheets1/2017/1/23/ultrafiltrationanoandro (Year: 2017).*
NPL Hamada et al. (in JAOCS 77(7):779-784, 2000). (Year: 2000).*
NPL mesh vs micron (Retrieved on Feb. 2019) (Year: 2019).*
NPL Takami et al. (in Appl. Microbiol Biotechnol. 30: 120-124, 1989). (Year: 1989).*
Slivinski et al., Braz. Arch. Biol. Technol., vol. 54, No. 3, pp. 559-568, 2011.

* cited by examiner

*Primary Examiner* — Bhaskar Mukhopadhyay
(74) *Attorney, Agent, or Firm* — Patterson Thuente Pedersen, P.A.

(57) ABSTRACT

A process for treating brewers spent grains for producing a high value protein product and a cellulosic residue, both from brewers spent grains that have not gone through fermentation. The high value protein product is useful as a protein supplement, or feed for livestock and poultry, and the cellulosic residue has value as a feedstock for a thermochemical process unit, such as for the production of a biofuel.

17 Claims, 1 Drawing Sheet

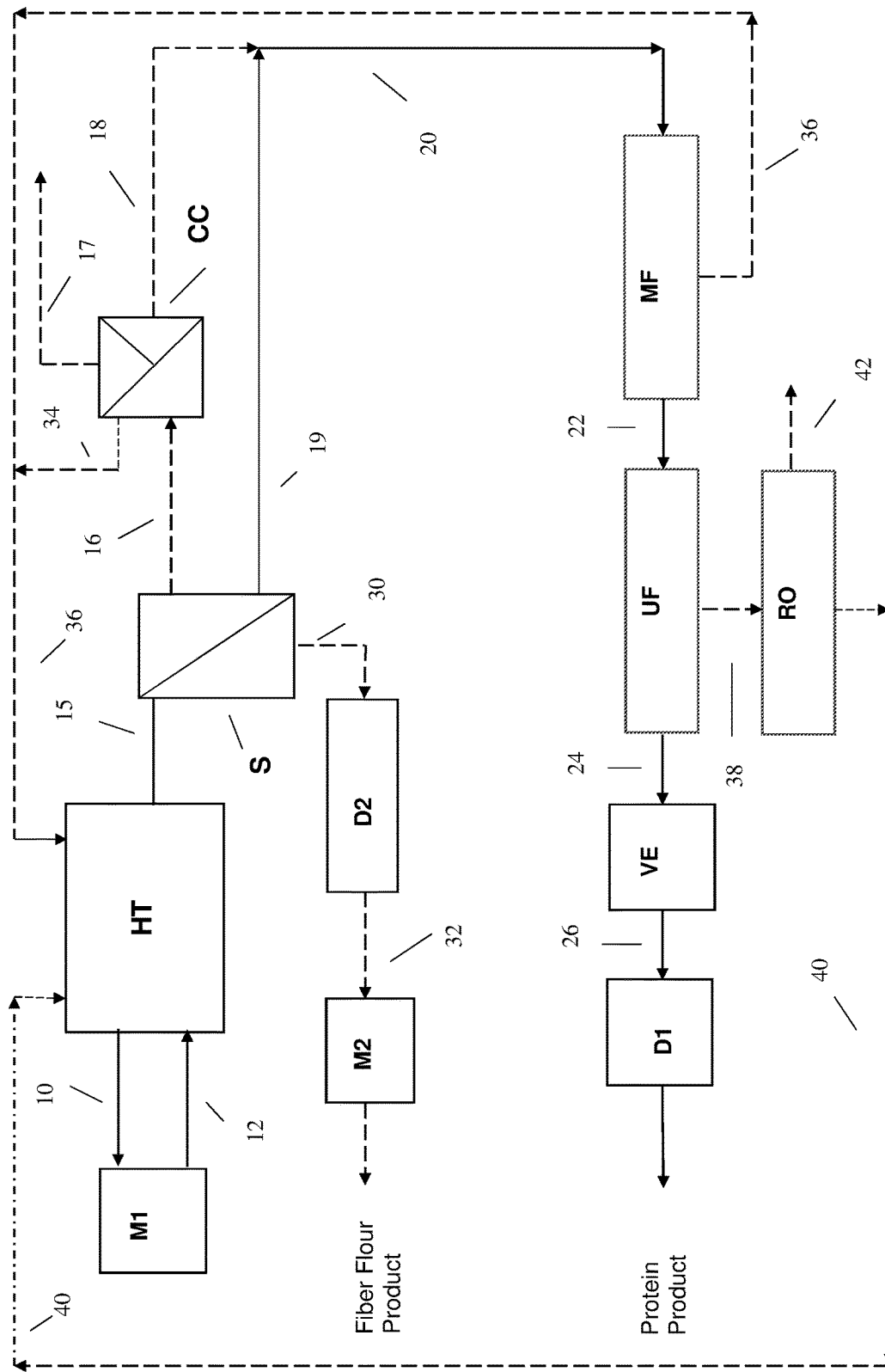

PROCESS FOR PRODUCING PROTEIN CONCENTRATE OR ISOLATE AND CELLULOSIC THERMOCHEMICAL FEEDSTOCK FROM BREWERS SPENT GRAINS

CROSS-REFERENCE TO RELATED APPLICATIONS

This application is a non-provisional application based on provisional application 62/447,383 filed Jan. 17, 2017.

BACKGROUND OF THE INVENTION

This invention relates to a process for treating brewers spent grains, that have not gone through fermentation, for producing a high value protein product and a cellulosic residue product. The high value protein product is useful as a protein supplement for human consumption, or feed for livestock and poultry. The cellulosic residue has value as a feedstock for a thermochemical process unit, such as for the production of a biofuel.

BACKGROUND OF THE INVENTION

Brewers spent grains (BSG) is the major by-product left after the processing of steeped, germinated, dried cereal gains (malt) for the production of beer and other malt products. Though barley is the primary grain used for brewing, beers can also be made from other grains such as wheat, rye, maize, rice, oats, sorghum and millet. In general, BSG represents about 85% of the total by-products generated. BSG can generally be defined as a lignocellulosic material containing inter alia, water, cellulose, non-cellulosic polysaccharides, lignin, crude proteins, and crude fats. BSG is available in large quantities throughout the year, but its main application has been limited to animal feeding. Since BSG still contain proteins, there is a significant interest in the brewing industry to further process the BSG to obtain more valued products, particularly for human consumption.

Also, a substantial amount of research and development is being done to reduce our dependency on petroleum-based energy and to move us toward more sustainable and environmentally friendly energy sources, such as wind energy, solar energy, and biomass. The conversion of biomass into transportation and other fuels is of great interest for reducing reliance on fossil fuels. Many biomass conversion technologies employ thermochemical processes, such as pyrolysis and gasification that have relatively high capital and operating costs. In particular, sourcing and preparing biomass feedstocks, such as wood and agricultural residues, such as corn stover and soybean hulls, for pyrolysis or gasification, typically result in marginal production economics.

While conventional processes have met with varying degrees of commercial success in obtaining higher value products from brewers spent grains there is still a need for improving efficiency and economics. One such desired product is a high protein content product for human consumption.

SUMMARY OF THE INVENTION

In accordance with the present invention there is provided a process for producing a protein product, and a cellulosic product suitable as a feedstock for thermochemical processing, from brewers spent grains having a protein content and a starch content and not having been subjected to fermentation, which process comprises:

a) introducing into a hydrolysis tank, with constant stirring, a mixture comprised of: i) brewers spent grains having a protein content and a starch content, and which has not gone through fermentation, and ii) an amount of water so that the ratio of water to grains is from about 8:1 to 11:1;

b) adding an effective amount of glucoamylase to the heated mixture, which effective amount is at least that amount that will lead to the conversion of at least 90 wt. % of the starch to sugars;

c) heating said mixture to a temperature from about 30° to about 70° C.;

d) cycling said heated mixture to and from the hydrolysis vessel to a particle size reduction stage wherein the size of grain particles, in said mixture, is reduced to about 500µ;

e) maintaining the temperature of about 30° C. to 70° C. with stirring for an effective amount of time to allow at least about 95 wt % of the starch from the grains to be converted to sugars;

f) adjusting the pH of the mixture to a level from about 7 to 10.5;

g) adding an effective amount of an alkaline protease enzyme to the mixture, which effective amount will be at least that amount required to solubilize at least about 80 wt. % of the proteins;

h) maintaining the pH of about 7 to 10.5 until the degree of protein hydrolysis is between 1 to 10:

i) raising the temperature to an effective temperature to deactivate the alkaline protease enzyme, thereby resulting in an intermediate product stream;

j) conducting said intermediate product stream to a liquid/solids separation stage resulting in a liquid stream and a solids-containing stream;

k) conducting said liquid stream to a microfiltration stage capable of removing solids greater than 20 to 500 kDa and resulting in a permeate liquid stream and solids-containing retentate stream;

l) subjecting permeate from the microfiltered liquid stream to ultrafiltration capable of removing solids smaller than 500 to 1500 daltons and resulting in a liquid stream comprised of about 10 wt. % to 50 wt. % solids with those solids having a protein content of 60 wt. % to about 90 wt. %;

m) conducting the liquid stream comprised of about 10-50 wt % solids to an evaporation stage wherein at least a fraction of any remaining water is driven off to produce a product comprised of at least about 80 wt % to about 90 wt. % protein.

BRIEF DESCRIPTION OF THE FIGURE

The FIGURE hereof is a flow diagram illustrating one preferred embodiment of the present invention. The dashing process lines in the FIGURE hereof represent other optional embodiments for practicing the present invention.

DETAILED DESCRIPTION OF THE INVENTION

Any brewers spent grains can be used in the practice of the present invention as long as it has not been subjected to fermentation. Non-limiting examples of such grains include barley, wheat, rye, maize, rice, oats, sorghum and millet. Most preferred is barley.

The present invention can be better understood with reference to the FIGURE hereof. The instant process is generally practiced by introducing, into hydrolysis tank HT, wet brewers spent grains and an effective amount of water to achieve a ratio of water to grains, on a dry weight basis of 8:1 to 11:1. It is preferred that the ratio of water to grains be from about 9:1 to 10:1. Brewers spent grains received from the brewer are typically received in a wet condition. The ratio of water to grains for wet grains received directly from a brewer will typically be from about 3:1 to about 6:1, more typically from about 3.5:1 to about 5:1. Thus, water will need to be added to achieve the desired ratio of water to grains for the process of this invention. Hydrolysis tank HT can also be referred to as a hydrolysis tank since proteins and starches are extracted from the grains by hydrolysis. Tank HT can be constructed from any suitable material, preferably a stainless steel and be open at the top or enclosed with a suitable cover containing ports for allowing entry of water, grains, and any other ingredient or reactant needed to practice the present invention. Hydrolysis tank HT will also contain a stirring apparatus (not shown) of suitable corrosion resistant material to constantly stir the mixture during the instant process.

While brewers spent grains received from a brewer will typically be in the pH range of about 3.5 to 6.5, if they are not the pH can easily be adjusted to that range. The adjustment will typically need to be done by lowering the pH to that range using a suitable acid. A preferred pH range for the mixture at this phase of the process is about 3.5 to 6.5. The acid used to lower the pH can be any suitable acid that is capable of achieving the desired pH range. The acid can be either an inorganic acid, preferably hydrochloric acid, or an organic acid, such as a carboxylic acid. The acidic mixture is then heated to a temperature from about 30° C. to about 70° C., preferably about 40° C. to about 60° C. and about 0.1 wt. % to about 5 wt. %, preferably about 0.15 wt. % of glucoamylase, on a dry weight basis is added. It will be understood that the terms "mixture" and "slurry" can be used interchangeably herein. It will be understood that it is not critical to the instant process that the glucoamylase be added after the mixture is heated. For example, the glucoamylase can be added and then the mixture heated to 30° C. to 70° C.

The mixture is continuously cycled to and from particle size reduction zone M1 via lines 10 and 12. A particle size reduction stage is also sometimes referred to herein as a milling stage. Any suitable particles size reduction equipment can be used that is capable of reducing the size of particles in an aqueous mixture or slurry, preferably at a water to grains ratio of 8:1 to 11:1. It is preferred that a colloid mill or rotor stator type of mill be used. More preferred is high-shear rotor-stator wet milling equipment. Rotor-stator wet milling equipment is well known in the art and can be commercially obtained from such companies as Kady International having a facility in Scarborough, Me.; Custom Milling & Consulting Inc having a facility in Fleetwood, Pa.; or Chemineer having a facility in Dayton, Ohio. The aqueous mixture is milled for an effective amount of time. That is, for that amount of time that will result in the average particle size of grains in the mixture to be less than about 500 microns (μ). This amount of time will typically be from about 30 minutes to about 60 minutes, preferably for about 45 minutes. The temperature and pH are maintained during this step to hydrolyze at least a fraction of any remaining starch. The hydrolyzing process will typically take about 30 to 45 minutes which allows time to effectively mill the grains. The grains are most likely completely milled to the desired size in about 20 minutes, but extra time is preferred to allow as much starch in the grains to be converted to sugar. It is preferred that at least 90 wt. % of the starch is converted to sugar, more preferred is at least 95 wt. % be converted, and most preferably at least about 98 wt. %. It is also most preferred that substantially all of the starch be converted to sugars, that is, wherein only a very small percent, for example less than about 1 wt. %, more preferably less than about 0.5 wt. % is left unconverted.

The pH of the resulting mixture in hydrolysis tank HT is then adjusted to about 7 to 10.5, preferably from about 8 to 10, more preferably to about 8.5 to 9.5 with use of a suitable aqueous base solution. It is preferred that the base be an alkali or alkaline earth metal hydroxide, more preferably sodium hydroxide. A temperature of about 30° C. to about 70° C. is maintained during this step.

An effective amount of alkaline protease enzyme is added. By "effective amount" we mean at least that amount of alkaline protease enzyme that will be capable of solubilizing at least 80 wt. % of the proteins, preferably from about 80 wt. % to 90 wt. % of the proteins. This amount will typically be from about 0.1 wt. % to about 0.3 wt. %, preferably about 0.25 wt. %, on a dry weight basis, of an alkaline protease enzyme, preferably alcalase, is added while maintaining the pH between about 7 and 10.5 and temperature between about 30° C. and 70° C. until the degree of protein hydrolysis is between about 1 and 10, preferably between about 2 and 8, and more preferably between about 3 and 4.5.

At this point, the temperature is raised to an effective temperature capable of deactivating the alkaline protease enzyme, but not so high as to result in an undesirable effect. This temperature will be an effective temperature to cause deactivation of the enzyme. This temperature will typically be from about 75° C. to 100° C., preferably from about 80° C. to about 85° C. The mixture is then held at that temperature for an effective amount of time to ensure that the enzyme is deactivated. This effective amount of time will be from about 2.5 to about 30 minutes, preferably from about 5 to 20 minutes, more preferably about 15 minutes. This results in an intermediate liquid/solids product stream which is sent via line 15 to a liquids/solids separator S wherein a liquid phase, and a solids-containing phase separated. The resulting liquid stream contains, inter alia, proteins, ash, sugars, fiber, and fats/oils, which is preferably sent via lines 19 and 20 to microfiltration stage MF, preferably employing a suitable membrane capable of removing solids greater than about 20 to 500 kDa.

It is within the scope of this invention that instead of passing the liquid phase resulting from separation stage S directly to microfiltration stage MF the liquid phase can optionally be further clarified by sending it via line 16 to a 3-phase separator/clarifying centrifuge CC wherein an aqueous phase, an oil (fat) phase, and a solids-containing phase are each separated from the other two phases. 3-phase separators are well known in a variety of industries. For example, the petroleum industry uses 3-phase separators to separate a gas phase, an oil phase, and a water phase from a mixture of those phases. In the instant process, a suitable 3-phase separator can be used that is capable of separating two liquid phases from a solids phase. The resulting oil stream is sent for collection via line 17. The solids-containing phase contains insoluble solids as a suspension in an aqueous stream at about 10% solids and can optionally be recycled via lines 34 and 36 back to hydrolysis tank HT because they still contain a significant amount of protein that can undergo hydrolysis. The liquid, or aqueous stream (extract) can optionally be sent via lines 18 and 20 to microfiltration stage MF.

The retentate from microfiltration stage MF will contain a significant amount of high molecular weight proteins, as well as fiber material and fats/oils and can optionally be recycled via line 36 to hydrolysis tank HT for additional protein removal. The resulting permeate from microfiltration stage MF is conducted via line 22 to ultrafiltration stage comprising a suitable ultrafiltration membrane wherein solids less than about 500 to 1500 Daltons (Da), preferably from about 800 to about 1000 Da are passed through. The term Da is well known in the art and is used as a measure of molecular weight or mass. For example, one hydrogen atom has a mass of 1 Da. Proteins and other macromolecule molecular weights are usually measured in kDa or kilodaltons wherein 1 kDa is 1000 Da (Daltons).

The retentate from ultrafiltration stage UF will be comprised of a high level of proteins and is passed via line 24 to evaporation stage VE which is preferably under a vacuum wherein the solids (protein) concentration of the stream is increased. The stream exiting evaporation stage VE is passed via line 26 to first drying stage D1 that preferably results in final protein powder product. Any suitable drying technology will work including drum dryers, ring dryers, fluidized bed dryers, vacuum tray dryers, conveyor dryers, and other technologies that reduce the water content of the final product to less than 10% moisture. Additionally, the final product can be a high-solids (>40 wt %) liquid instead of a dry powder. This liquid can be produced by any suitable dewatering technology including the previously discussed ultrafiltration membrane, vacuum evaporator, thin film evaporator, or other suitable water removal technology. The permeate from ultrafiltration stage UF is optionally passed via line 38 to reverse osmosis stage RO comprised of a suitable osmosis membrane material so that clean, low solids water can be recycle back to hydrolysis tank HT via line 40 for water conservation purposes. The clean water is the permeate from unit RO. The retentate from reverse osmosis unit RO is preferably disposed of as wastewater via line 42. The RO membrane will have pores from about 100 to 500 Daltons, so everything larger than that will be removed from the water stream.

The solids-containing stream from liquids/solids separator stage S is sent via line 30 to second drying stage D2 wherein substantially all remaining water is driven off and the resulting dried solids, which is primarily comprised of cellulosic material, is sent via line 32 to milling stage M2 and milled into a fiber flour product.

It is within the scope of this invention that it be practiced in what is referred to as the Insoluble Protein Concentrate Process. In this process wet (as received) BSG is mixed with water to achieve an 8:1 to 11:1, preferably a 9:1 water to grain on a dry weight ratio. This mixture is heated to a temperature from about 50° C. to about 60° C., preferably to about 55° C. and glucoamylase is added at a 0.1 to 0.2%, preferably at 0.15% on the dry weight basis. This mixture is milled in situ and simultaneously stirred for 30 minutes to about 60 minutes, preferably for about 45 minutes. The solids are separated from the liquid and dried to produce an insoluble protein concentrate. The liquid stream is concentrated and dried to produce a sweet, carbohydrate source. The following additional embodiments are within the scope of this invention with respect to the Insoluble Protein Concentrate Process: a) prior to adding additional water, dry the grains and use a mild milling process to separate the husk from the rest of the grains and separate from the grains. Continue the process as normal after husk removal; and b) an alpha-amylase and/or beta-amylase step is included during the glucoamylase step to increase the starch hydrolysis of branched chains.

Alternative hydrolysis conditions can include: temperatures from about 10° C. to about 100° C., preferably from about 20° C. to about 80° C., more preferably from about 30° C. to about 70° C. and most preferably from about 40° C. to about 60° C.; and times from about 30 minutes to 180 minutes, preferably from about 60 minutes to about 150 minutes, and more preferably from about 90 minutes to about 130 minutes.

In another embodiment, the grains are milled to an average particle size from about 0.05 mm to about 0.5 mm, preferably from about 0.05 mm to about 0.3 mm. At least a fraction of the protein is extracted from the milled grains with use of a basic aqueous solution at effective extraction conditions. The basic component is preferably provided by a hydroxide of a metal selected from Groups 1 and 2 of the Periodic Table of the Elements. Preferred metals include sodium, potassium, magnesium and calcium, with sodium and potassium being the more preferred and sodium being the most preferred. By effective extraction conditions we mean at a pH of 10 to 12, preferably about 10.5 to 11.5, more preferably at a pH of 11; at a temperature range of about 20° C. to about 60° C.; and with a grains to basic solution ratio of 1:5 to 1:10. The resulting basic spent grains mixture can then be conducted to a separation zone wherein the fraction containing dissolved proteins is separated from a protein-lean (<15% protein by weight) cellulosic grains residue fraction. It is preferred that the separation be done using a centrifuge. The protein fraction is preferably spray dried resulting in a substantially dry protein product. The protein-lean cellulosic grains residue is collected where it can be marketed as a livestock feed component or as a feedstock component for a subsequent thermochemical process, such as pyrolysis or gasification which can be used for the production of biofuel, preferably a transportation fuel, preferably a distillate fuel. The protein product obtained by the practice of the present invention is a protein concentrate or preferably a protein isolate comprised of at 80 wt. % protein.

In one preferred embodiment, the treated spent grains be subjected to an effective amount of ultrasonic energy to improve the efficiency of the protein extraction portion of the process. The preferred effective ultrasonic energy input is from about 3 to about 30 Joules/gram of grains with a frequency of about 40 kHz with about 3 to about 10 Joules/gram being preferred.

The following additional embodiments are also within the scope of this invention; i) the use of a debittering exo-peptidase prior to the drying step at a pH between 6.5-9 and a temperature of 45° C. to about 65° C. for 30 to 120 minutes to reduce protein bitterness; ii) the use of a debittering exo-peptidase during the alcalase addition step to reduce protein bitterness; iii) performing the milling step prior to the addition of glucoamylase, iv) include the addition of alpha-amylase and/or beta-amylase during the glucoamylase addition step to increase starch hydrolysis of branched chains; v) separate the water from the grains immediately following the glucoamylase addition step which removes the glucose from the process prior to solubilizing the protein, then add additional water to the grains to bring the water to grains ratio back to 9:1 and continue the process as normal; vi) the use of a mild milling to separate the husk from the rest of the grains, then separate from the grains and continue the process as normal after husk removal; and vii) during the glucoamylase addition step, add an effective amount of glucose oxidase, which will oxidize the glucose to form hydrogen peroxide which will lighten the color of the end products and reduce the glucose content, then continue the process as normal.

Also within the scope of this invention is a brewery process wherein a cereal grain is processed to produce a beer and leaving a substantial amount of spent grains as a by-product. The spent grains are then processed in accordance with the process herein described for obtaining a concentrated protein product and a cellulosic product from the spent grains. Conventional beer making steps typically require that a cereal grain, preferably barley, be prepared for brewing by a process involving malting, heating, drying out, and cracking open the husks of the kernels of the grains, which helps expose the starches during the mashing process. In mashing, the grains are steeped in hot, but not boiling water for an effective amount of time, typically about an hour. This activates enzymes in the grains to cause the break-down of starch into sugars. Once this is done, the water is drained from the mash, which is now rich in sugar. A sticky, sweet liquid referred to as "wort" is produced. Wort is often referred to as unmade beer. The wort consists primarily of sugars and water resulting from mashing. At this point lautering can be used to separate the wort from spent grains as efficiently as possible. Once the wort has been separated from the grains in what is called the lauter-tun, the process described herein can be performed using the lautertun as the extraction tank. The lautertun has a false bottom with a screen that can act as the 60 micron screen previously described. It also contains a stirring mechanism.

The wort is boiled for an effective amount of time then hops and other spices are added. Hops provide bitterness to balance out the sugar in the wort and provide flavor. Once the wort is cooled, strained, and filtered and put into a fermentation vessel yeast is added. At this point the brewing is complete and fermentation begins. The beer is stored for a few weeks at cold temperatures in the case of lagers, while the yeast works its magic by eating up the sugar and producing carbon dioxide and alcohol and waste products. The resulting beer can then be conditioned so it can mature and become smooth and by-products of fermentation diminished. The beer can also be subjected to secondary fermentation.

What is claimed is:

1. A process for extracting a protein product and a cellulosic product suitable as a feedstock for thermochemical processing from brewers spent grains by hydrolysis, the brewers spent grains having a protein content and a starch content and not having been subjected to fermentation, which process comprises:
    a) introducing into a hydrolysis vessel, with constant stirring, a mixture comprised of: i) brewers spent grains having a protein content and a starch content, and which has not gone through fermentation, and ii) an amount of water so that the ratio of water to grains is from about 8:1 to 11:1;
    b) adding an effective amount of glucoamylase to the mixture, which effective amount is at least that amount that will lead to the conversion of at least 90 wt. % of the starch to sugars;
    c) heating said mixture to a temperature from about 30° to about 70° C.;
    d) cycling said heated mixture to and from the hydrolysis vessel to a particle size reduction stage wherein the size of grain particles, in said mixture, is reduced to about 500 μm;
    e) maintaining the temperature of about 30° C. to 70° C. with stirring for an effective amount of time to allow at least about 95 wt. % of the starch from the grains to be converted to sugars;
    f) adjusting the pH of the mixture to a level from about 8.5 to 9.5;
    g) adding an effective amount of an alkaline protease enzyme to the mixture, which effective amount will be at least that amount required to solubilize at least about 80 wt. % of the proteins;
    h) maintaining the pH of about 8.5 to 9.5 until the degree of protein hydrolysis is between 1 to 10;
    i) raising the temperature to an effective temperature to deactivate the alkaline protease enzyme, thereby resulting in an intermediate product stream;
    j) conducting said intermediate product stream to a liquid/solids separation stage resulting in a liquid stream and a solids-containing stream which is dried to produce a cellulosic residue product that is suitable as a fiber feed source;
    k) conducting the liquid stream resulting from the liquid/solids separation stage to a 3-phase separation stage, wherein an aqueous stream, a stream containing oils and fats, and a solids stream are produced;
    l) conducting said aqueous stream to a microfiltration stage capable of removing solids greater than 20 to 500 kDa and resulting in a permeate liquid stream and solids-containing retentate stream;
    m) subjecting the permeate liquid stream to ultrafiltration capable of removing solids smaller than 500 to 1500 daltons and resulting in a liquid stream comprised of about 10 wt. % to 50 wt. % solids with those solids having a protein content of 60 wt. % to about 90 wt. %; and
    n) conducting the liquid stream comprised of about 10-50 wt % solids to an evaporation stage wherein at least a fraction of any remaining water is driven off to produce a product comprised of at least about 80 wt. % to about 90 wt. % protein.

2. The process of claim 1 wherein the grains of the brewers spent grains is selected from the group consisting of barley, wheat, rye, maize, rice, oats, sorghum and millet.

3. The process of claim 2 wherein the brewers spent grains are spent barley grains.

4. The process of claim 1 wherein the ratio of water to grains is about 9:1 to about 10:1.

5. The process of claim 1 wherein the particle size reduction is performed with a rotor stator mill.

6. The process of claim 1 wherein the pH of the mixture formed in the hydrolysis tank is about 3.5 to about 6.5.

7. The process of claim 1 wherein the temperature of the mixture of step c) hereof is from about 40° C. to about 60° C.

8. The process of claim 1 wherein the degree of hydrolysis is from about 2 to 8.

9. The process of claim 8 wherein the degree of hydrolysis is from about 3 to 4.5.

10. The process of claim 1 wherein at least 98 wt. % of the starch is converted to sugars.

11. The process of claim 1 wherein the alkaline protease enzyme is alcalase.

12. The process of claim 1 wherein the temperature of enzyme reaction is from about 75° C. to about 95° C.

13. The process of claim 1 wherein the microfiltration membrane removes proteins and solids greater than about 300 to 500 kDa.

14. The process of claim 1 wherein the product from the evaporation stage is dried to produce a protein product.

15. The process of claim 1 wherein the solids stream from the liquids/solids separator is dried and milled to produce a fiber flour product.

16. The process of claim 1, wherein the solids stream from the 3-phase separation stage is conducted back to the hydrolysis tank.

17. A process for extracting a protein product and a cellulosic product suitable as a feedstock for thermochemical processing from brewers spent grains by hydrolysis, the brewers spent grains having a protein content and a starch content and not having been subjected to fermentation, which process comprises:
- a) introducing into a hydrolysis vessel, with constant stirring, a mixture comprised of: i) brewers spent grains having a protein content and a starch content, and which has not gone through fermentation, and ii) an amount of water so that the ratio of water to grains is from about 8:1 to 11:1;
- b) adding an effective amount of glucoamylase to the mixture, which effective amount is at least that amount that will lead to the conversion of at least 90 wt. % of the starch to sugars;
- c) heating said mixture to a temperature from about 30° to about 70° C.;
- d) cycling said heated mixture to and from the hydrolysis vessel to a particle size reduction stage wherein the size of grain particles, in said mixture, is reduced to about 500 μm;
- e) maintaining the temperature of about 30° C. to 70° C. with stirring for an effective amount of time to allow at least about 95 wt. % of the starch from the grains to be converted to sugars;
- f) adjusting the pH of the mixture to a level from about 8.5 to 9.5;
- g) adding an effective amount of an alkaline protease enzyme to the mixture, which effective amount will be at least that amount required to solubilize at least about 80 wt. % of the proteins;
- h) maintaining the pH of about 8.5 to 9.5 until the degree of protein hydrolysis is between 1 to 10;
- i) raising the temperature to an effective temperature to deactivate the alkaline protease enzyme, thereby resulting in an intermediate product stream;
- j) conducting said intermediate product stream to a liquid/solids separation stage resulting in a liquid stream and a solids-containing stream which is dried to produce a cellulosic residue product that is suitable as a fiber feed source;
- k) conducting the liquid stream resulting from the liquid/solids separation stage to a 3-phase separation stage wherein an aqueous stream, a steam containing oils and fats, and a solids stream are produced;
- l) conducting said aqueous stream to a microfiltration stage capable of removing solids greater than 20 to 500 kDa and resulting in a permeate liquid stream and solids-containing retentate stream;
- m) subjecting the permeate liquid stream to ultrafiltration capable of removing solids smaller than 500 to 1500 daltons and resulting in a liquid stream comprised of about 10 wt. % to 50 wt. % solids with those solids having a protein content of 60 wt. % to about 90 wt. %;
- n) conducting the liquid stream comprised of about 10-50 wt. % solids to an evaporation stage wherein at least a fraction of any remaining water is driven off to produce a product comprised of at least about 80 wt. % to about 90 wt. % protein; and
- o) conducting the solids stream from the 3-phase separation stage back to the hydrolysis tank.

* * * * *